United States Patent
Björck et al.

(10) Patent No.: US 10,126,312 B2
(45) Date of Patent: Nov. 13, 2018

(54) DIAGNOSTIC METHOD FOR URINARY TRACT INFECTION

(71) Applicant: Hansa Medical AB, Lund (SE)

(72) Inventors: Lars Björck, Lund (SE); Bertil Christensson, Lund (SE); Heiko Herwald, Veberod (SE); Adam Linder, Lund (SE); Per Åkesson, Lund (SE)

(73) Assignee: Hansa Medical AB, Lund (SE)

( * ) Notice: Subject to any disclaimer, the term of this patent is extended or adjusted under 35 U.S.C. 154(b) by 0 days.

(21) Appl. No.: 15/153,570

(22) Filed: May 12, 2016

(65) Prior Publication Data

US 2016/0252529 A1 Sep. 1, 2016

Related U.S. Application Data

(62) Division of application No. 13/983,224, filed as application No. PCT/EP2012/052059 on Feb. 7, 2012.

(30) Foreign Application Priority Data

Feb. 7, 2011 (GB) .................................. 1102108.6

(51) Int. Cl.
| | |
|---|---|
| G01N 33/53 | (2006.01) |
| G01N 33/68 | (2006.01) |
| G01N 33/569 | (2006.01) |
| A61K 45/06 | (2006.01) |
| C07K 16/18 | (2006.01) |

(52) U.S. Cl.
CPC ......... *G01N 33/6893* (2013.01); *A61K 45/06* (2013.01); *C07K 16/18* (2013.01); *G01N 33/569* (2013.01); *C07K 2317/33* (2013.01); *G01N 2400/40* (2013.01); *G01N 2800/348* (2013.01)

(58) Field of Classification Search
None
See application file for complete search history.

(56) References Cited

U.S. PATENT DOCUMENTS

| | | | |
|---|---|---|---|
| 5,420,016 | A | 5/1995 | Boguslaski et al. |
| 5,627,262 | A | 5/1997 | Pereira |
| 5,962,241 | A | 10/1999 | Ax et al. |
| 5,976,536 | A | 11/1999 | Stephens et al. |
| 6,303,321 | B1 | 10/2001 | Tracey et al. |
| 7,655,480 | B2 | 2/2010 | Pereira |
| 7,767,395 | B2 | 8/2010 | Garrett et al. |
| 8,518,648 | B2 | 8/2013 | Bjorck |
| 2003/0170745 | A1 | 9/2003 | Pereira |
| 2004/0197930 | A1 | 10/2004 | Rosenfeld |
| 2005/0196817 | A1 | 9/2005 | Kingsmore et al. |
| 2006/0173162 | A1 | 8/2006 | Djurup et al. |
| 2007/0092911 | A1 | 4/2007 | Buechler et al. |
| 2007/0110804 | A1 | 5/2007 | Royer |
| 2007/0166768 | A1 | 5/2007 | Pereira |
| 2007/0269437 | A1 | 11/2007 | Djurup et al. |
| 2009/0221021 | A1 | 9/2009 | Chalumeau et al. |
| 2014/0080754 | A1 | 3/2014 | Bjorck |
| 2014/0080925 | A1 | 3/2014 | Björck et al. |
| 2014/0187503 | A1 | 7/2014 | Bjorck |

FOREIGN PATENT DOCUMENTS

| | | |
|---|---|---|
| WO | WO 1995/028949 | 11/1995 |
| WO | WO 1998/032390 | 7/1998 |
| WO | WO 2000/047104 | 8/2000 |
| WO | WO 2003/076459 A1 | 9/2003 |
| WO | WO 2004/016653 A2 | 2/2004 |
| WO | WO 2004/088324 A2 | 10/2004 |
| WO | WO 2004/112713 A2 | 12/2004 |
| WO | WO 2005/028512 A1 | 4/2006 |
| WO | WO 2007/045873 A2 | 4/2007 |
| WO | WO-2007/045873 A2 | 4/2007 |
| WO | WO 2007/068830 A1 | 6/2007 |
| WO | WO 2008/151808 A1 | 12/2008 |
| WO | WO-2008/151808 A1 | 12/2008 |
| WO | WO 2012/038541 A1 | 3/2012 |
| WO | WO 2012/107450 A1 | 8/2012 |

OTHER PUBLICATIONS

Nousbaum et al (Hepatology vol. 45, issue 5,2007).*
Behling-Kelly et al., (2006) "Roles of cellular activation and sulfated glycans in Haemophilus somnus adherence to bovine brain microvascular endothelial cells," *Infection and Immunity* 74(9):5311-5318.
Beran et al., (2010) "Heparin-binding Protein as a Biomarker of Circulatory Failure during Severe Infections: A Report of Three Cases," *Scandinavian Journal of Infectious Diseases* 42:634-636.
Bochud et al., (2004) "Antimicrobial therapy for patients with severe sepsis and septic shock: An evidence-based review," *Crit Care Med.* 32(11 Suppl.):S495-S512.
Bossink et al., (1999) "The Clinical Host Response to Microbial Infection in Medical Patients with Fever," *Chest* 116(2):380-390.
Claessens (2007) "Diagnosis and Treatment of Severe Sepsis," *Critical Care* 11 (Suppl 5):1-8.
Gautam et al., (2001) "Heparin-Binding Protein (HBP/CAP37): A Missing Link in Neutrophil-Evoked Alteration of Vascular Permeability," *Nat Med.* 7(10):1123-1127.
Lennard et al., (1982) "Implications of Leukocytosis and Fever at Conclusion of Antibiotic Therapy for Intra-abdominal Sepsis," *Ann Surg.* 195(1):19-24.
Linder et al., (2009) "Heparin-Binding Protein: An Early Marker of Circulatory Failure in Sepsis," *Clin Infect Dis.* 49(7):1044-1150.
Linder et al., (2010) "Roles of Heparin-Binding Protein in Bacterial Infections," *Journal of Innate Immunity* 2:431-438.

(Continued)

*Primary Examiner* — Tracy Vivlemore
*Assistant Examiner* — Carmencita M Belei
(74) *Attorney, Agent, or Firm* — Dechert LLP (57) ABSTRACT

It has been demonstrated that the urinary level of HBP increases in individuals that have a urinary tract infection. Accordingly, the urinary level of HBP in an individual can be used to determine whether or not an individual has a urinary tract infection.

9 Claims, 4 Drawing Sheets
Specification includes a Sequence Listing.

(56) References Cited

OTHER PUBLICATIONS

Linder et al., (2011) "Heparin-binding Protein: A Diagnostic Marker of Acute Bacterial Meningitis," *Critical Care Medicine* 39(4):812-817.
Mariscalco et al., (2011) "Heparin-binding Protein: Another Neutrophil Granule Protein . . . Another New Biomarker?," *Critical Care Medicine* 39(4):910-912.
O'Grady et al., (1999) "Detection of Macrophage Inflammatory protein (MIP)-1α and MIP-1β during Experimental Endotoxemia and Human Sepsis," *J Infect Dis.* 179:136-141.
Serruto et al., 2010, "Neisseria Meningitidis GNA2132, A Heparin-Binding Protein that Induces Protective Immunity in Human," *Proc. Natl. Acad. Sci USA.* 107(8):3770-3775.
PCT International Search Report from PCT/EP2008/004743 dated Nov. 11, 2008.
PCT International Preliminary Report on Patentability for PCT/EP2008/004743, dated Nov. 8, 2009.
PCT International Search Report from PCT/EP2011/066611 dated Jan. 9, 2012.
Reining et al., (2001) *Nat Med.* 7:S87.
Tapper et al., (2002) "Secretion of Heparin-binding Protein from Human Neutrophils is determined by its Localization in Azurophilic Granules and Secretory Vesicles," *Blood* 99(5): 1785-1793.
Soehnlein et al., (2005) "Neutrophil-derived heparin-binding protein (HBP/CAP37) deposited on endothelium enhances monocyte arrest under flow conditions," *J Immunol.* 174(10):6399-405.
UK Intellectual Property Office Search Report from GB0711327.7 dated Aug. 22, 2007.
UK IPO Search Report from GB1016161.0 dated Apr. 15, 2011.
Weiss et al., (2003)"Transient Leukocytosis, Granulocyte Colony-Stimulating Factor Plasma Concentrations, and Apoptosis Determined by Binding of Annexin V by Peripheral Leukocytes in Patients with Severe Sepsis," *Ann N.Y Acad. Sci.* 1010:742-747.
Wolpe et al., (1989) "Macrophage Inflammatory proteins 1 and 2: Members of a Novel Superfamily of Cytokines," *FASEB J.* 3:2565-2573.
Yoshida et al., (2008) "Expression of the Heparin-Binding Growth Factor Midkine in the Cerebrospinal of Patients with Neurological Disorders," *Internal Medicine* 47(2):83-89.
Kjölvmark et al., 2012, "Elevated Urine Levels of Heparin-Binding Protein in Children with Urinary Tract Infection," *Pediatr Nephrol* 27(8):1301-1308, XP007920418.
PCT International Search Report from PCT/EP2012/052059 dated Dec. 4, 2012.
Mussap et al., 2006, "Laboratory Investigation for the Early Diagnosis and Monitoring of Neonatal Urinary Tract Infections: the Present Situation and Future Perspectives," *Journal of Chemotherapy* 18(3):9-13, XP009157721.
Kahn et al., 2002, "Contact-System Activation in Children with Vasculitis" National Library of Medicine Abstract No. 12241658.
Wang et al., 2006, "Specific Cleavage of Insulin-like Growth Factor-Binding Protein-1 by a Novel Protease Activity," *Cellular and Molecular Life Sciences* 63(19-20):2405-2414, XP019440764.
Woodford et al., 2011, "Diagnosis and Management of Urinary Infections in Older People," *Clinical Medicine, Royal College of Physicians*11(1):80-83, XP009157720.
Pereira et al., 1989, "Quantitation of cationic antimicrobial granule protein of human polymorphonuclear leukocytes by ELISA," *J Immunological Methods* 117:115-120.
Peltola et al., (2006) "Comparison of total white blood cell count and serum C-reactive protein levels in confirmed bacterial and viral infections," *J Peds* 149(5):721-724.

\* cited by examiner

DIAGNOSTIC METHOD FOR URINARY TRACT INFECTION

CROSS REFERENCE TO RELATED APPLICATIONS

This application is a divisional of U.S. application Ser. No. 13/983,224, filed Nov. 19, 2013, which is a national stage of International Application No. PCT/EP2012/052059, filed Feb. 7, 2012, which claims priority under 35 U.S.C. 119(a)-(d) and 365(b) to United Kingdom Application No. 1102108.6, filed Feb. 7, 2011, the contents of all of which are incorporated herein in their entireties by reference thereto.

REFERENCE TO SEQUENCE LISTING, TABLE OR COMPUTER PROGRAM

The official copy of the Sequence Listing is submitted concurrently with the specification as an ASCII formatted text file via EFS-Web, with a file name of "381181-003.txt", a creation date of May 12, 2016, and a size of 2.13 kilobytes. The Sequence Listing filed via EFS-Web is part of the specification and is incorporated by reference herein in its entirety.

FIELD OF THE INVENTION

The invention relates to the diagnosis and treatment of urinary tract infection.

BACKGROUND OF THE INVENTION

Urinary tract infection (UTI) is a common diagnosis that can result in serious complications in both children and adults. Efficient diagnosis and treatment is important to reduce the risk of renal failure and overuse of antibiotics. Rapid and safe diagnostic methods are required as an alternative to bacterial cultures. Early treatment improves prognosis of urinary tract infection, and therefore early diagnosis is vital. A reliable biological or clinical marker to determine as early as possible whether or not an individual has a urinary tract infection is needed.

SUMMARY OF THE INVENTION

Heparin-binding protein (HBP, CAP37, Azurocidin) is a glycosylated, single chain, positively charged 37 kDa inactive serine protease homologue exhibiting 44% sequence identity with human neutrophil elastase. The three dimensional structure of HBP has been published (Iversen et at Nat Struct Biol. 1997 April; 4(4):265-8). It is contained in the azurophilic granulae and secretory vesicles of human neutrophils (Lindmark et al, J Leukoc Biol 1999; 66(4):634-43 and Tapper et al, Blood 2000; 96:2329-2337). It is a multifunctional protein that has been shown to induce vascular leakage by altering the $Ca^{2+}$ balance of the blood vessel cytoskeleton (Gautam et al, Nature Medicine 2001; 7(10): 1123-7). The M-protein of group A *streptococci* (GAS) in complex with fibrinogen has been shown to induce HBP release by stimulation of the B2-integrin receptor of neutrophils (Herwald et al, Cell 2004; 116(3):367-79). LPS can also induce HBP release by an unknown mechanism (Rasmussen et al, FEBS Lett 1996; 390(1):109 12). The sequence of HBP is publically available (for example as NCBI accession no. NP 001691 REGION: 27 ... 248) and is reproduced below as SEQ ID NO. 1

SEQ ID NO: 1
IVGGRKARPRQFPFLASIQNQGRHFCGGALIHARFVMTAASCFQSQNPGV
STVVLGAYDLRRRERQSRQTFSISSMSENGYDPQQNLNDLMLLQLDREAN
LTSSVTILPLPLQNATVEAGTRCQVAGWGSQRSGGRLSRFPRFVNVTVTP
EDQCRPNNVCTGVLTRRGGICNGDGGTPLVCEGLAHGVASFSLGPCGRGP
DFFTRVALFRDWIDGVLNNPGP

Urinary HBP levels in patients suspected of having a urinary tract infection have not previously been investigated. The inventors have shown for the first time that levels of HBP are increased in individuals with urinary tract infection. According to the invention there is thus provided a method of identifying whether or not an individual has urinary tract infection, which method comprises measuring HBP in the individual and thereby determining whether or not the individual has urinary tract infection.

The invention further provides:

an agent for the detection of HBP for use in determining whether or not an individual has a urinary tract infection;

a test kit for use in a method for determining whether or not an individual has a urinary tract infection, which test kit comprises an agent for the detection of HBP in an individual;

a method of treating an individual for urinary tract infection comprising:
(i) determining whether or not an individual has a urinary tract infection using a method of the invention; and
(ii) administering to an individual identified in (i) as at risk, a therapeutically effective amount of at least one agent suitable for the treatment of urinary tract infection.

DETAILED DESCRIPTION OF THE INVENTION

Diagnosis

The present invention relates to a method of identifying whether or not a subject has a urinary tract infection. The invention therefore relates to the diagnosis of urinary tract infection.

The present inventors have for the first time investigated the level of urinary HBP in patients suspected of having urinary tract infection. The inventors have demonstrated that urinary HBP levels are elevated in patients with urinary tract infection relative to those who do not have urinary tract infection.

The individual under test is typically suspected of having a urinary tract infection. The individual is typically a mammal. The mammal is typically a human or a domestic mammal such as a horse, a cow, a sheep, a dog or a cat. The individual is preferably a human.

The individual under test may have one or more symptoms associated urinary tract infections including for example fever, typically greater than 37.5° C., abdominal or back pain, and/or a positive nitrite test.

The level of HBP is typically measured in vitro in a sample obtained from an individual. The sample typically comprises a body fluid of an individual. A fluid sample may be a sample of blood, plasma, serum, urine, cerebrospinal fluid or joint fluid. The sample is preferably a urine sample.

According to the present invention, an increased level or concentration of HBP compared with the baseline level or concentration indicates that the individual has a urinary tract infection. The baseline level is typically the level of HBP in an individual who does not have a urinary tract infection, or who is suspected of having a urinary tract infection, but is subsequently confirmed to not have a urinary tract infection. Thus the method according to the present invention may include comparison of the level of HBP in the sample to that of a baseline level.

In accordance with the present invention the concentration of HBP is greater than 15 ng/ml, preferably greater than 25 ng/ml, more preferably greater than 30 ng/ml, more preferably greater than 32 ng/ml, more preferably greater than 35 ng/ml, and most preferably greater than 50 ng/ml in the sample. Such levels can be used to indicate that an individual has a urinary tract infection.

In an alternative aspect, the method may comprise assessing the relative level or concentration of HBP in the sample compared to a baseline level or concentration. Typically, a method wherein the level or concentration of HBP in the sample is increased by at least 3 fold or 4 fold relative to the baseline level or concentration of HBP is indicative of urinary tract infection.

Other markers may also be included in the analysis such as the white blood cell count (WBC), particularly the urine WBC, and/or IL-6. HBP may also be used in combination with the nitrite test.

Detection of HBP

The invention is typically carried out by measuring the level of HBP in vitro in a sample obtained from the individual. The sample typically comprises a body fluid of the individual. A fluid sample may be a sample of blood, plasma, serum, urine, cerebrospinal fluid or joint fluid. The sample is preferably a urine sample.

The sample may be processed prior to being assayed, for example by centrifugation. The sample may also be typically stored prior to assay, preferably below −70° C.

Standard methods known in the art may be used to assay the level of HBP. These methods typically involve using an agent for the detection of HBP. The agent typically binds specifically to HBP. The agent may be an antibody specific for HBP, an aptamer that binds to HBP, a serine proteinase inhibitor such as aprotinin, for example as described in Petersen et al, Eur J Biochem 1993; 271-9, or a soluble fragment of an integrin, for example as described in Cai and Wright, S. D. J Exp Med 1996; 184:213-23. By specific, it will be understood that the agent or antibody binds to HBP with no significant cross-reactivity to any other molecule, particularly any other protein. For example, an agent or antibody specific for HBP will show no significant cross-reactivity with human neutrophil elastase. Cross-reactivity may be assessed by any suitable method.

An antibody used in the method of the invention may either be a whole antibody or a fragment thereof which is capable of binding to HBP. The antibody may be monoclonal. Such a whole antibody is typically an antibody which is produced by any suitable method known in the art. For example, polyclonal antibodies may be obtained by immunising a mammal, typically a rabbit or a mouse, with HBP under suitable conditions and isolating antibody molecules from, for example, the serum of said mammal. Monoclonal antibodies may be obtained by hybridoma or recombinant methods.

Hybridoma methods involve immunising a mammal, typically a rabbit, a rat or a mouse, with HBP under suitable conditions, then harvesting the spleen cells of said mammal and fusing them with myeloma cells. The mixture of fused cells is then diluted and clones are grown from single parent cells. The antibodies secreted by the different clones are then tested for their ability to bind to HBP, and the most productive and stable clone is then grown in culture medium to a high volume. The secreted antibody is collected and purified.

Recombinant methods involve the cloning into phage or yeast of different immunoglobulin gene segments to create libraries of antibodies with slightly different amino acid sequences. Those sequences which give rise to antibodies which bind to HBP may be selected and the sequences cloned into, for example, a bacterial cell line, for production.

Typically the antibody is a mammalian antibody, such as a primate, human, rodent (e.g. mouse or rat), rabbit, ovine, porcine, equine or camel antibody. The antibody may be a camelid antibody or shark antibody. The antibody may be a nanobody. The antibody can be any class or isotype of antibody, for example IgM, but is preferably IgG.

The fragment of whole antibody that can be used in the method comprises an antigen binding site, e.g. Fab or F(ab)2 fragments or ScFV. The whole antibody or fragment may be associated with other moieties, such as linkers which may be used to join together 2 or more fragments or antibodies. Such linkers may be chemical linkers or can be present in the form of a fusion protein with the fragment or whole antibody. The linkers may thus be used to join together whole antibodies or fragments which have the same or different binding specificities, e.g. that can bind the same or different polymorphisms. The antibody may be a bispecific antibody which is able to bind to two different antigens, typically any two of the polymorphisms mentioned herein. The antibody may be a 'diabody' formed by joining two variable domains back to back. In the case where the antibodies used in the method are present in any of the above forms which have different antigen binding sites of different specificities then these different specificities are typically to polymorphisms at different positions or on different proteins. In one embodiment the antibody is a chimeric antibody comprising sequence from different natural antibodies, for example a humanised antibody.

Methods to assess HBP level typically involve contacting a sample with an agent or antibody capable of binding specifically to HBP. Such methods may include dipstick assays and Enzyme-linked Immunosorbant Assay (ELISA). Typically dipsticks comprise one or more antibodies or proteins that specifically bind HBP. If more than one antibody is present, the antibodies preferably have different non-overlapping determinants such that they may bind to HBP simultaneously.

ELISA is a heterogeneous, solid phase assay that requires the separation of reagents. ELISA is typically carried out using the sandwich technique or the competitive technique. The sandwich technique requires two antibodies. The first specifically binds HBP and is bound to a solid support. The second antibody is bound to a marker, typically an enzyme conjugate. A substrate for the enzyme is used to quantify the HBP-antibody complex and hence the amount of HBP in a sample. The antigen competitive inhibition assay also typically requires an HBP-specific antibody bound to a support. An HBP-enzyme conjugate is added to the sample (containing HBP) to be assayed. Competitive inhibition between the HBP-enzyme conjugate and unlabeled HBP allows quantification of the amount of HBP in a sample. The solid supports for ELISA reactions preferably contain wells.

The present invention may also employ antibodies to HBP in direct sensing techniques including but not limited to those based upon surface plasmon resonance, surface acoustic wave, quartz crystal microbalance, microcalorimetry or electrochemical impedance spectroscopy.

The present invention may also employ methods of measuring HBP that do not comprise antibodies. High Performance Liquid Chromatography (HPLC) separation and fluorescence detection is preferably used as a method of determining the HBP level. HPLC apparatus and methods as described previously may be used (Tsikas D et al. J Chromatogr B Biomed Sci Appl 1998; 705:174-6) Separation during HPLC is typically carried out on the basis of size or charge. Prior to HPLC, endogenous amino acids and an internal standard L-homoarginine are typically added to assay samples and these are phase extracted on CBA cartridges (Varian, Harbor City, Calif.). Amino acids within the samples are preferably derivatized with o-phthalaldehyde (OPA). The accuracy and precision of the assay is preferably determined within quality control samples for all amino acids.

The invention further provides a diagnostic kit that comprises means for measuring the HBP level in an individual and thereby determining whether or not the individual has a urinary tract infection. The kit typically contains one or more antibodies that specifically bind HBP. For example, the kit may comprise a monoclonal antibody, a polyclonal antibody, a single chain antibody, a chimeric antibody, a CDR-grafted antibody or a humanized antibody. The antibody may be an intact immunoglobulin molecule or a fragment thereof such as a Fab, $F(ab')_2$ or Fv fragment. If more than one antibody is present, the antibodies preferably have different non-overlapping determinants such that they may bind to HBP simultaneously.

The kit may additionally comprise means for the measurement of other laboratory or clinical parameters. For example the kit may comprise means for measuring the WBC count in an individual, and/or the level or concentration of one or more of urinary nitrite, IL-6, glucose, protein and plasma C-reactive protein.

The kit may additionally comprise one or more other reagents or instruments which enable any of the embodiments of the method mentioned above to be carried out. Such reagents or instruments include one or more of the following: suitable buffer(s) (aqueous solutions), means to isolate HBP from sample, means to obtain a sample from the individual (such as a vessel or an instrument comprising a needle) or a support comprising wells on which quantitative reactions can be done. The kit may, optionally, comprise instructions to enable the kit to be used in the method of the invention or details regarding which individuals the method may be carried out upon.

Therapy

The present invention also relates to the treatment of an individual identified by a method of the invention as having a urinary tract infection. Thus, a substance for use in the treatment of a urinary tract infection may be used in the manufacture of a medicament for use in the treatment of an individual identified by a method of the invention as having a urinary tract infection. The condition of an individual identified by a method of the invention as having a urinary tract infection can therefore be improved by administration of such a substance. A therapeutically effective amount of a substance useful for the treatment of a urinary tract infection may be given to an individual identified by a method of the invention as in need thereof. Substances suitable for the treatment of a urinary tract infection typically include one or more antibiotics.

The following Example illustrates the invention:

EXAMPLE

Methods
Study Population

This prospective study included 78 individuals (26 male and 52 female), who were admitted to the Department of Paediatric Diseases, the Hospital of Helsingborg, Sweden, between March and June 2009. The criteria for inclusion of patients in the study were fever (temperature≥37.5° C.) or symptoms suggesting urinary tract infection, abdominal or back pain in older individuals and nonspecific signs such as irritability or difficulties in feeding in younger children. Urinary tract infection included both lower urinary tract infection and pyelonephritis. Patients with neutropenia (neutrophils≤$0.5 \times 10^9$/L) or patients who had received antibiotics in the previous 72 hours were excluded. The project protocol was approved by the ethics committee of Lund University Hospital and consent was obtained from all patients by their parents. Patients were divided into the following groups: 1) Patients with a final diagnosis of urinary tract infection, based on bacterial culture, a urine sample with a single microorganism at ≥$10^5$ colony-forming-units (CFU)/ml and typical clinical symptoms. 2) Patients with suspected urinary tract infection, based on clinical characteristics or a urine sample with a single microorganism≥$10^3$ CFU/ml, or a positive nitrite test. The lower cut off value for bacteriuria is based on recommendations from Swedish Institute for Infectious Disease Control. 3) Patients with fever, but non-urinary tract infection 4) Patients without fever, and no urinary tract infection.

Clinical and Laboratory Evaluations

Body temperature was recorded and CRP was analysed in plasma. Urine was collected with midstream (75 samples) samples or suprapubic aspiration (2 samples). In one patient the technique was not registered. Analyses of urine samples were done with bacterial cultures and dipstick tests, containing tests for nitrite, white blood cells (WBC), albumin, red blood cells and glucose. Dipsticks (Multisticks® 7, Siemens) were analysed on a Clinitek Status (Bayer Health Care). Nitrite was presented as either positive or negative, and WBC as semi-quantitative values in a graded scale: 0<15 leukocytes/pt urine, 1≥15 leukocytes/µL urine, 2≥70 leukocytes/µL urine, 3≥125 leukocytes/µL urine, 4≥500 leukocytes/µL urine. For determination of HBP levels, urine was centrifuged within one hour of the sampling, and aliquots of the supernatants were stored at −70° C. until analysis. The concentration of HBP was determined by enzyme-linked immunosorbent assay (ELISA). Microtiter plates (NUNC) were coated with a mouse monoclonal antibody directed against HBP in coating buffer (0.05M $NaHCO_3$, pH 9.6). Plates were washed with phosphate-buffered saline and blocked with bovine serum albumin (Sigma). Urine samples were diluted 1/40 in sample buffer (1M NaCl), added to the wells in duplicate, and incubated for 30 min at 37° C. Each plate also contained calibration samples of known concentration of recombinant HBP. After washing, plates were incubated with a polyclonal rabbit antiserum towards HBP diluted 1/7000. Bound antibodies were detected by incubation with peroxidase-conjugated antibody against rabbit IgG, Bio-Rad (1/3000). The level of HBP in each patient sample was determined by calculating the mean optical densities of duplicates which were correlated to the results from the standard curve. Levels of IL-6 in urine were analysed with a sandwich-ELISA, (ELISA MAX™ Deluxe Sets), according to the manufacture's description. Urine samples were diluted 1/2 in incubation buffer, and analysed in duplicates.

Statistical Analysis

Comparisons between groups were made by the non-parametric Kruskal-Wallis test and Mann-Whitney-U-test for continuous variables with skewed distributions. Correlations were made by Spearman's non-parametric test. Areas under receiver-operator characteristic curves were used to illustrate the power of HBP, IL-6, U-WBC and nitrite. Sensitivity, specificity, positive and negative predictive value were calculated for HBP, IL-6 and U-WBC. The level of statistical significance was defined as two-tailed p-value<0.05. The SPSS 17.0 software system (SPSS) was used for statistical analyzes.

Results

Characteristics of the Patients and Laboratory Signs

Seventy eight individuals were enrolled in the study. The age of the patients ranged from 1 month to 18 years (mean 5.96 years) and 75% were older than 1 year. Ten patients were diagnosed with urinary tract infection (2 with lower urinary tract infection and 8 with pyelonephritis), and all had *Escherichia coli* in the urine culture (group 1). Five patients had a suspected urinary tract infection based on characteristic symptoms or laboratory results indicating urinary tract infection (group 2). Three of these 5 patients had only a moderate growth of *Escherichia coli* or beta-hemolytic *Streptococci* group B in urine ($\geq 10^3$-$\leq 10^5$ CFU/ml), one patient had typical clinical symptoms of cystitis but were not cultured and had a negative dipstick test, and one patient had characteristic signs of pyelonephritis with a negative urine culture and a dipstick test that was positive for nitrite. Thirty patients had fever but no laboratory or clinical signs of urinary tract infection (group 3). Their urine cultures were negative or had mixed strains of bacteria (indicative of sample contamination). Thirty-three patients had no fever and no laboratory signs of urinary tract infection (group 4). Their urine cultures were negative. Some of these had diagnoses (known before entering the study) like enuresis, Alport syndrome, Henoch-Schonlein-syndrome and nephrotic syndrome.

Statistical Analysis of Results from Plasma and Urine

Figure 1:
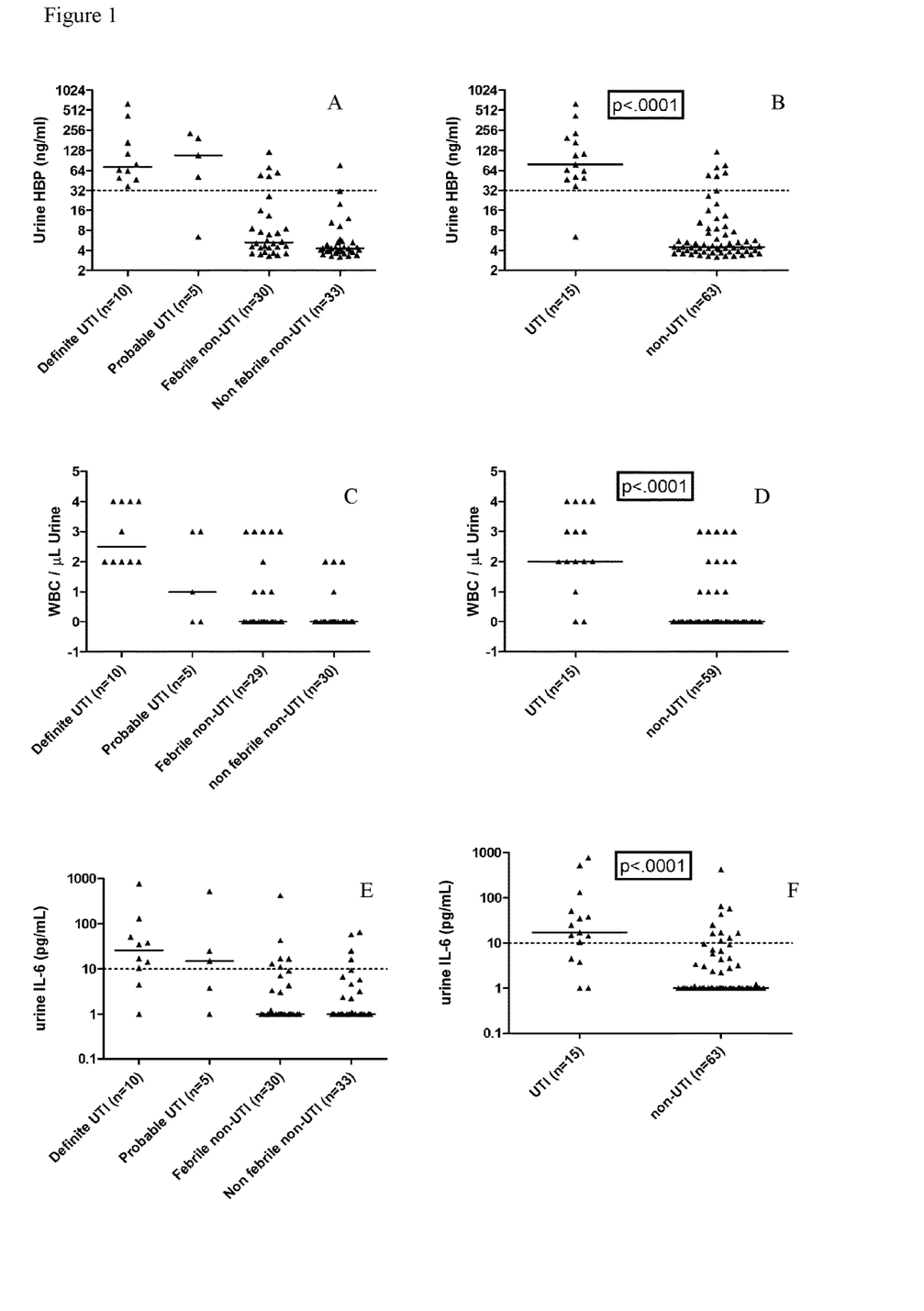
FIG. 1 shows Urine levels of HBP, U-WBC and IL-6. Each dot represents the concentration in an individual urine sample of HBP (A and B), WBC (C and D) and IL-6 (E and F). The four patients groups are described in the Methods section. Bars represent median of values. The suggested cut-off value for HBP is marked at 32 ng/ml, for WBC at 2 WBC/µL and for IL-6 10 pg/mL.
Figure 2:
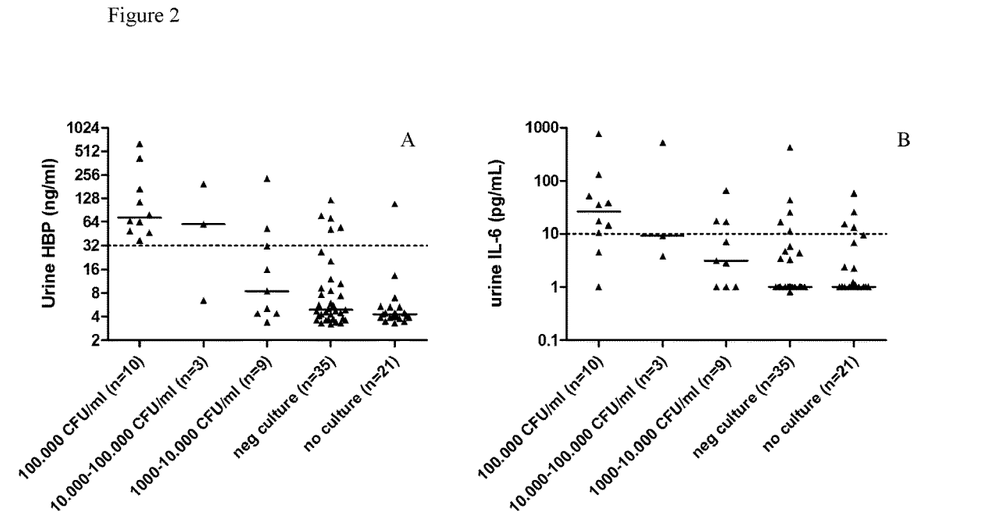
FIG. 2 shows Urinary levels of HBP and IL-6 correlated to concentrations of bacteria in urine Each dot represents the concentration in an individual urine sample of HBP (A) and IL-6 (B). Bars represent median of values.
Figure 3:
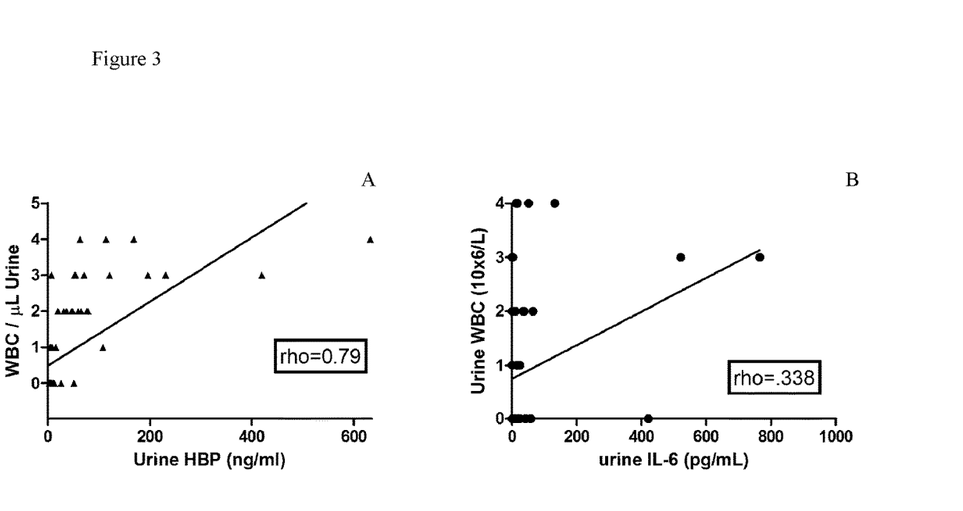
FIG. 3 shows correlation between HBP and WBC in urine, and between IL-6 and U-WBC in urine. Spearman's rank correlation coefficient (rho)=0.79 indicate that there is a correlation between levels of HBP and WBC in urine (A). Spearman's rank correlation coefficient for IL-6 is 0.338. Each dot represents the concentration in an individual urine sample of HBP, WBC and IL-6.

There were no significant differences in median age, gender, temperature, CRP in plasma, HBP in urine, IL-6 in urine, WBC or nitrite in urine between group 1 (urinary tract infection) and 2 (suspected urinary tract infection). Plasma CRP and urinary glucose did not result in any significant differences between any groups. Urinary albumin had significant differences between group 1 and 3 (fever, non-urinary tract infection), 1 and 4 (no fever, non infection), 2 and 3, but not between the others. Urinary red blood cells had significant differences between group 1 and 3, 1 and 4 but not between the others. There were significant differences in median levels of HBP, IL-6 and WBC in urine between group 1 and 3. Also comparison of group 1 and 4 had significantly different median levels of HBP, IL-6 and WBC in urine. There were significant differences in the urine levels of HBP, IL-6 and WBC between group 1 combined with group 2 as compared to group 3 combined with group 4. (FIG. 1 A-F). An interesting implication was that urine with high concentrations of bacteria ($\geq 10^5$ CFU/ml) seemed to have higher levels of HBP and WBC compared to urine with less or no bacteria (FIG. 2 A-B). Spearman's test with a rank correlation coefficient (rho)=0.79 indicated a relatively strong correlation between levels of HBP and WBC in urine (FIG. 3). IL-6 did not have this strong correlation with WBC in urine, (rho=0.38).

Figure 4:
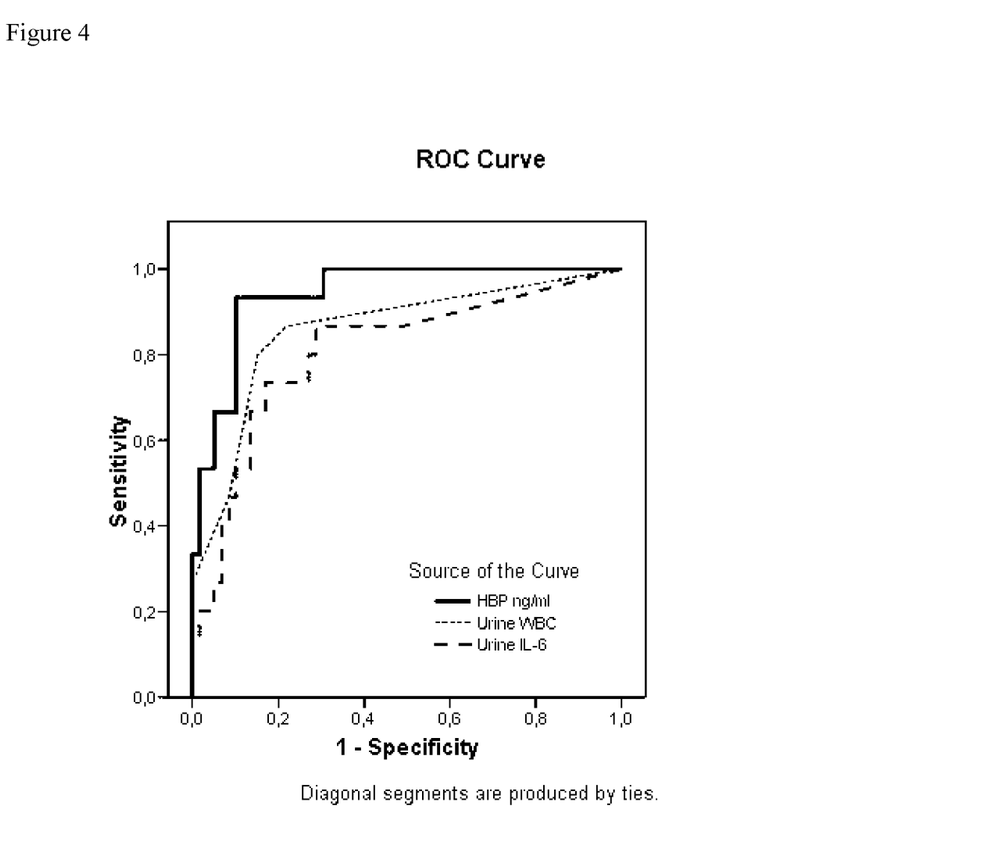
FIG. 4 shows Receiver-operating characteristics curves (ROC) of HBP and WBC in urine differentiating between UTI and no UTI. Areas under the ROC curves (AUC) were 0.942 (95% confidence interval, 0.889-0.996) for HBP, 0.808 (95% confidence interval, 0.675-0.941) for IL-6, 0.858 (95% confidence interval, 0.742-0.974) for WBC.

For calculation of sensitivity, specificity, positive predictive value and negative predictive value group 1 and 2 was combined, referred to urinary tract infection-group and compared to the combined groups 3 and 4, referred to non-urinary tract infection. Using a cut-off level of HBP of ≥32 ng/ml, the sensitivity and specificity in diagnosing urinary tract infection were 93.3% and 90.3% respectively. HBP in urine had the highest sensitivity compared to WBC, nitrite and IL-6. HBP in urine also had the highest specificity compared to WBC and IL-6 (Table 2). Nitrite had the best specificity compared to the other markers. Based on the 19.2% prevalence of urinary tract infection in this study the positive and negative predictive values of HBP for prediction of urinary tract infection were 70.0% and 98.3%, respectively (Table 2). ROC curves demonstrated that HBP in urine was the best predictor of urinary tract infection with an area under curve (AUC) value of 0.94 compared to U-WBC and IL-6 (FIG. 4).

DISCUSSION

Urinary tract infection can have serious consequences and antibiotic resistance is a growing issue. Therefore, tests with higher sensitivity and specificity are needed. Several previous studies have investigated biomarkers in urine for the detection of urinary tract infection, like IL-6, lactoferrin, IL-8, TNF-α, elastase and Clara cell protein. HBP in plasma has been studied as a biomarker for sepsis in adults, and data suggested that a normal plasma level of HBP in febrile patients with suspected infection could with high probability (negative predictive value 94.5%) rule out the risk of developing severe sepsis. In the present study, concentrations of HBP in urine was compared with urinary IL-6, nitrite, WBC, red blood cells, albumin, glucose and plasma CRP. HBP in urine had a higher AUC value (0.94) than IL-6, nitrite and WBC, and was thus the best predictor for urinary tract infection. HBP in urine had a high negative predictive value (98.3%), and could thus rule out disease with a high probability. The nitrite test has its limitations with a low sensitivity. Some bacterial species can not transform nitrate to nitrite, for example *Staphylococcus saprophyticus* and *Enterococcus*. Other reasons for false negative nitrite are short incubation time of urine in the bladder and intake of high doses of vitamin C. Outliers in the study exist. In group 2 (suspected urinary tract infection), one patient with symptoms of pyelonephritis and beta-hemolytic *Streptococci* group-B in the urine culture ($10^4$-$10^5$ CFU/ml) had a low level of HBP (6.3 ng/ml). This patient was also negative in the rapid test for urinary nitrite and WBC. Urine HBP levels were higher in patients with urinary tract infection than in patients with other kinds of infections, which indicates that HBP release in urine is dependent on the activation of white blood cells by for instance bacterial infection in urine.

TABLE 1

Patient Characteristics. Clinical and laboratory data.
Median, range and P-values for age, gender, CRP, HBP, temperature, U-WBC and nitrite.

|  | Group 1 (n = 10) | Group 2 (n = 5) | Group 3 (n = 30) | Group 4 (n = 33) | P-value x | P-value xx | P-value xxx |
|---|---|---|---|---|---|---|---|
| Age (years) | 4.5 (0-17) | 7.36 (0-16) | 2.0 (0-17) | 8.1 (0-18) | 0.322 | 0.225 | 0.299 |
| Gender(female/male) | 9/1 | 4/1 | 23/7 | 16/17 | 0.604 | 0.367 | 0.021 |
| HBP (ng/ml) | 72.1 (37.0-632.2) | 108.3 (6.4-230.9) | 5.3 (3.3-121.2) | 4.3 (3.2-76.5) | 1.00 | 0.000 | 0.000 |
| U-WBC[1] (WBC/µL) | 3 (2-4) | 1 (0-3) | 0 (0-3) | 0 (0-2) | 0.077 | 0.000 | 0.000 |
| Nitrite (pos/neg)[2] | 1 (0-1) | 0 (0-1) | 0 (0-0) | 0 (0-0) | 0.077 | 0.000 | 0.000 |
| Temperature (° C.) | 37.9 (36.7-40.0) | 38.5 (37.3-41.1) | 38.2 (37.0-41.1) | 37.0 (36.9-39.4) | 0.297 | 0.171 | 0.000 |
| CRP (ng/ml) | 146 (0-201) | 165 (10-184) | 56 (0-190) | 16 (0-169) | 0.322 | 0.152 | 0.013 |

NOTE:
P-values analyzed with the Mann-Whitney test.
x = Group 1 vs 2,
xx = Group 1 vs 3,
xxx = Group 1 vs 4
[1]Semi-quantitative scale: 0 < 15 leukocytes/µL, 1 ≥ 15 leukocytes/µL, 2 ≥ 70 leukocytes/µL, 3 ≥ 125 leukocytes/µL, 4 ≥ 500 leukocytes/µL
[2]Positive nitrite was defined as 1 and negative nitrite was defined as 0.

TABLE 2

Sensitivity, Specificity, PPV and NPV of HBP, U-WBC and nitrite for predicition of UTI. (Cutoff Values of 32 ng/mL for HBP, 10 pg/mL for IL-6, 2 for U-WBC, 100 ng/ml for CRP, 0.5 for nitrite, 38° C. for temperature).

|  | Sensitivity, % | Specificity, % | PPV, % | NPV, % |
|---|---|---|---|---|
| HBP | 93.3 | 90.3 | 70.0 | 98.3 |
| IL-6 | 73.3 | 84.1 | 52.4 | 93.0 |
| U-WBC | 80.0 | 84.8 | 57.1 | 94.3 |
| Nitrite | 53.3 | 100 | 100 | 89.4 |
| CRP | 64.3 | 72.7 | 50 | 82.8 |
| Temperature | 53.3 | 63.3 | 23.7 | 84.4 |

PPV, positive predictive value,
NPV, negative predictive value.

The invention claimed is:

1. A method of treating an individual having a urinary tract infection (UTI), comprising:
   measuring the level of Heparin Binding Protein (HBP, CAP37, Azuricidin) in a urine sample obtained from an individual by;
   (i) contacting the sample with an antibody which binds specifically to HBP; and
   (ii) quantitating the amount of antibody-HBP complex to measure the HBP level in the urine sample;
   detecting the presence of UTI in the individual at about 93% Sensitivity or greater and at about 90% Specificity or greater based on the measured HBP level in the urine sample; and administering to the individual detected as having UTI an effective amount a therapeutic agent suitable for treating UTI.

2. The method of claim 1, wherein the individual is a mammal.

3. The method of claim 2, wherein the mammal is a human.

4. The method of claim 3, wherein the detecting of UTI at about 93% Sensitivity or greater and at about 90% Specificity or greater is determined by a Receiver Operating Characteristic (ROC).

5. The method of claim 3, wherein the 93% Sensitivity and the 90% Specificity for detecting UTI is a threshold value of about 32 ng/ml in the urine sample.

6. The method of claim 1, wherein the binding of the antibody to HBP is measured by enzyme linked immunosorbent assay (ELISA).

7. The method of claim 1, wherein the binding of the antibody to HBP is measured using a dipstick assay.

8. The method of claim 1, wherein the urinary tract infection is lower urinary tract infection or pyelonephritis.

9. The method of claim 1, further comprising determining white blood cell count or level of IL6 in a urine sample from the individual, or conducting a nitrite test on a urine sample from the individual.

* * * * *

SEQUENCE LISTING

<160> NUMBER OF SEQ ID NOS: 1

<210> SEQ ID NO 1
<211> LENGTH: 222
<212> TYPE: PRT
<213> ORGANISM: homo sapiens

<400> SEQUENCE: 1

Ile Val Gly Gly Arg Lys Ala Arg Pro Arg Gln Phe Pro Phe Leu Ala
1               5                   10                  15

Ser Ile Gln Asn Gln Gly Arg His Phe Cys Gly Gly Ala Leu Ile His
                20                  25                  30

Ala Arg Phe Val Met Thr Ala Ala Ser Cys Phe Gln Ser Gln Asn Pro
            35                  40                  45

Gly Val Ser Thr Val Val Leu Gly Ala Tyr Asp Leu Arg Arg Arg Glu
        50                  55                  60

Arg Gln Ser Arg Gln Thr Phe Ser Ile Ser Ser Met Ser Glu Asn Gly

-continued

```
                65                  70                  75                  80
Tyr Asp Pro Gln Gln Asn Leu Asn Asp Leu Met Leu Leu Gln Leu Asp
                85                  90                  95

Arg Glu Ala Asn Leu Thr Ser Ser Val Thr Ile Leu Pro Leu Pro Leu
            100                 105                 110

Gln Asn Ala Thr Val Glu Ala Gly Thr Arg Cys Gln Val Ala Gly Trp
            115                 120                 125

Gly Ser Gln Arg Ser Gly Gly Arg Leu Ser Arg Phe Pro Arg Phe Val
        130                 135                 140

Asn Val Thr Val Thr Pro Glu Asp Gln Cys Arg Pro Asn Asn Val Cys
145                 150                 155                 160

Thr Gly Val Leu Thr Arg Arg Gly Gly Ile Cys Asn Gly Asp Gly Gly
                165                 170                 175

Thr Pro Leu Val Cys Glu Gly Leu Ala His Gly Val Ala Ser Phe Ser
            180                 185                 190

Leu Gly Pro Cys Gly Arg Gly Pro Asp Phe Phe Thr Arg Val Ala Leu
        195                 200                 205

Phe Arg Asp Trp Ile Asp Gly Val Leu Asn Asn Pro Gly Pro
210                 215                 220
```